(12) United States Patent
Hendriks et al.

(10) Patent No.: US 11,564,582 B2
(45) Date of Patent: Jan. 31, 2023

(54) IMPLANT DEVICE FOR IN-BODY MONITORING

(71) Applicant: KONINKLIJKE PHILIPS N.V., Eindhoven (NL)

(72) Inventors: Cornelis Petrus Hendriks, Eindhoven (NL); Mark Thomas Johnson, Eindhoven (NL); Achim Rudolf Hilgers, Eindhoven (NL); Franciscus Johannes Gerardus Hakkens, Eindhoven (NL); Daan Anton Van Den Ende, Eindhoven (NL); Manfred Müller, Eindhoven (NL); Arjen Van Der Horst, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 416 days.

(21) Appl. No.: 16/772,632

(22) PCT Filed: Dec. 14, 2018

(86) PCT No.: PCT/EP2018/085090
§ 371 (c)(1),
(2) Date: Jun. 12, 2020

(87) PCT Pub. No.: WO2019/115819
PCT Pub. Date: Jun. 20, 2019

(65) Prior Publication Data
US 2020/0383583 A1 Dec. 10, 2020

(30) Foreign Application Priority Data

Dec. 15, 2017 (EP) .................................. 17207607
Sep. 7, 2018 (EP) .................................. 18193231

(51) Int. Cl.
*A61B 5/026* (2006.01)
*A61B 5/07* (2006.01)
(Continued)

(52) U.S. Cl.
CPC .............. *A61B 5/026* (2013.01); *A61B 5/076* (2013.01); *A61B 5/6862* (2013.01); *B08B 7/02* (2013.01); *A61B 2560/0214* (2013.01)

(58) Field of Classification Search
None
See application file for complete search history.

(56) References Cited

U.S. PATENT DOCUMENTS

| 7,901,360 | B1 | 3/2011 | Yang et al. |
| 7,922,667 | B2 * | 4/2011 | Gianchandani ........... G01F 1/60 600/454 |

(Continued)

FOREIGN PATENT DOCUMENTS

WO 1998029030 A1 7/1998

OTHER PUBLICATIONS

Konyo, M., et al., "Development of velocity sensor using ionic polymer-metal composites", Proceedings of SPIE, Smart Structures and Materials 2004: Electroactive Polymer Actuators and Devices (EAPAD), vol. 5385, pp. 307-318, Jul. 27, 2004.
(Continued)

*Primary Examiner* — Shirley X Jian
(74) *Attorney, Agent, or Firm* — Schott, P.C.

(57) ABSTRACT

A monitoring system includes an implantable intra-vascular support device for positioning against a vessel wall and an implantable sensor-actuator mounted to the support device. The sensor-actuator is drivable between a non-deployed position in which it is against the support device and a deployed position in which it is displaced away from the support device. Sensor signals are generated when in the (Continued)

deployed position. This system is able to monitor flow away from the edge of a vessel by deploying the sensor-actuator towards the center of the vessel. When flow monitoring does not need to take place, it can be non-deployed so that it does not present an occlusion to the flow.

16 Claims, 1 Drawing Sheet

(51) Int. Cl.
*A61B 5/00* (2006.01)
*B08B 7/02* (2006.01)

(56) References Cited

U.S. PATENT DOCUMENTS

| | | | | |
|---|---|---|---|---|
| 8,298,148 | B2* | 10/2012 | Furman | A61B 8/12 |
| | | | | 600/374 |
| 10,660,528 | B2* | 5/2020 | Bailey | A61F 2/91 |
| 2002/0130673 | A1 | 9/2002 | Pelrine et al. | |
| 2004/0176672 | A1 | 9/2004 | Silver et al. | |
| 2005/0154321 | A1 | 7/2005 | Wolinsky et al. | |
| 2005/0186241 | A1 | 8/2005 | Boyle et al. | |
| 2005/0273014 | A1* | 12/2005 | Gianchandani | G01F 1/56 |
| | | | | 128/903 |
| 2005/0277839 | A1 | 12/2005 | Alderman et al. | |
| 2008/0154141 | A1 | 6/2008 | Shuros et al. | |
| 2008/0249379 | A1* | 10/2008 | Furman | A61B 5/0031 |
| | | | | 600/301 |
| 2013/0053711 | A1 | 2/2013 | Kotlanka et al. | |
| 2017/0086683 | A1 | 3/2017 | Bailey et al. | |

OTHER PUBLICATIONS

Griffiths, D., et al., "Development of ionic polymer transducers as flow shear stress sensors: Effects of electrode architecture", Proc. of SPIE, vol. 6529, pp. 65290L-1-65290L-9, Apr. 18, 2007.

Nagem, D. A. P., et al., "Ionic Polymer-Metal Composites Used as a Force Sensor", 20th International Congress of Mechanical Engineering, Proceedings of COBEM, Nov. 15-20, 2009.

Extended European Search Report issued in connection with corresponding EP Application No. 17207607.7 dated May 30, 2018.

International Search Report and Written Opinion issued in connection with corresponding PCT Application No. PCT/EP2018/085090 dated Mar. 13, 2019.

* cited by examiner

IMPLANT DEVICE FOR IN-BODY MONITORING

CROSS-REFERENCE TO RELATED APPLICATIONS

The present application is a U.S. National Phase application under 35 U.S.C. § 371 of International Application No. PCT/EP2018/085090, filed on Dec. 14, 2018, which claims the benefit of European Patent Application No. 17207607.7 filed on Dec. 15, 2017 and European Patent Application No. 18193231.0 filed on Sep. 7, 2018. These applications are hereby incorporated by reference herein.

FIELD OF THE INVENTION

This invention relates to implant devices for in-body monitoring.

BACKGROUND OF THE INVENTION

There is increasing demand for unobtrusive health sensing systems. In particular, there is a shift from conventional hospital treatment towards unobtrusive vital signs sensor technologies, centered around the individual, to provide better information about the subject's general health.

Such vital signs monitor systems help to reduce treatment costs by disease prevention and enhance the quality of life. They may provide improved physiological data for physicians to analyze when attempting to diagnose a subject's general health condition. Vital signs monitoring typically includes monitoring one or more of the following physical parameters: heart rate, blood pressure, respiratory rate and core body temperature.

By way of example, in the US about 30% of the adult population has a high blood pressure. Only about 52% of this population have their condition under control. Hypertension is a common health problem which has no obvious symptoms and may ultimately cause death, and is therefore often referred to as the "silent killer". Blood pressure generally rises with aging and the risk of becoming hypertensive in later life is considerable. About 66% of the people in age group 65-74 have a high blood pressure. Persistent hypertension is one of the key risk factors for strokes, heart failure and increased mortality.

The condition of the hypertensive patients can be improved by lifestyle changes, healthy dietary choices and medication. Particularly for high risk patients, continuous 24 hour blood pressure monitoring is very important and there is obviously a desire for systems which do not impede ordinary daily life activities.

It is known to provide implantable sensor devices for monitoring physiological parameters, such as blood pressure. While the initial insertion is an invasive procedure, once this is completed, the sensor remains in place for unobtrusive sensing for a prolonged period of time. Thus, implanted sensor technologies are also seen as minimally invasive (in the long term).

Implantable devices enable unobtrusive and long term monitoring of patients with chronic diseases such as heart failure, peripheral artery disease or hypertension. The purpose of monitoring is to provide reassurance or early warning indicators, but also to reduce or in general to control medication.

This invention relates more particularly to the monitoring of intravascular blood flow, for example after insertion of a stent or other vascular implant. In general there is a need to perform monitoring after stent placement to see if new problems might occur and to help in decisions on new interventions or medication use.

There are in fact various applications where intra-vascular flow measurement is of interest, and some of these are discussed below.

Stent patency is the state of being open and unblocked. For example, a common problem with coronary stents is "in-stent restenosis" (ISR), even with drug eluting stents. Follow-up after treatment is commonly implemented with computer tomography imaging. The disadvantage is the need for an X-ray dose, the need for a hospital visit, and the fact that it is only a point measurement in time. Instead it would be desirable to continuously monitor stent patency and to provide an early warning when necessary, or to reduce medicine when possible.

During Coronary Artery Bypass Graft (CABG) surgery, there is a need to know if the blood flow in the bypass is sufficient. This can be monitored for example with a cuff-like device which is placed around the graft during surgery. In general, the prospect for recovery is good: about 90% of patients experience significant improvements after coronary artery bypass graft surgery and for most people, the graft remains open for about 10-15 years. However, coronary artery bypass surgery does not prevent coronary artery disease from recurring. In 5-10% of coronary artery bypass graft surgeries, the bypass graft stops supplying blood to the bypassed artery within one year. About 40% of patients have a new blockage within 10 years after surgery and require a second bypass, change in medication, or an interventional procedure.

In order to provide reassurance, early warning, or optical (minimum) medication it desired to monitor the arterial bypass graft after the surgery, to check whether the blood flow does not drop below a certain value and to timely intervene if necessary.

Monitoring may also be used for active surveillance of indolent cancer. Cancer treatment can have negative side effects, for instance with prostate cancer. In such cases it might be considered to monitor the tumor at regular intervals with doctor visits and to treat only when the tumor starts to grow. Slow prostate growth may allow such a strategy. However, if there is too much time between the doctor visits this may give unrecorded metastasis. In this case continuous monitoring of the blood flow in and out the prostate can provide an indication for the tumor growth.

The "May Thurner syndrome" (MTS) is a condition in which compression of the common venous outflow tract of the left lower extremity may cause discomfort, swelling, pain or blood clots, called deep venous thrombosis (DVT). The problem is that the blood is not transported back to the upper body. Often it is unclear if or when stenting is needed. A temporary or a small unobtrusive sensor could provide decision support. This is important because MTS often concerns young people and a stent stays for life; the stent may also cause damage or deformation of this important vessel. A sensor may also be used to enable diagnosis during walking (whereas diagnosis in the hospital is in lying position). A small and local sensing implant might be acceptable if it can prevent unnecessary implantation of a big stent.

It may also be of interest to measure the flow in a dialysis shunt. A shunt is an artificial loop (plastic tube) between an artery and a vein in the forearm with an access point to an external dialysis circuit. For timely intervention it is desirable to know or predict when the flow drops below a certain level. Currently the flow is monitored externally for example three times each week during dialysis based on the pre-pump arterial pressure. Between dialysis, the shunt resistance can be subjectively monitored by the patient via tactile methods (sense the vibration of blood going through the arm), or by a physician using a stethoscope. However, clotting or shunt compression for example during sleep might be acute and continuous quantitative flow monitoring would safeguard the shunt.

Thus, there are many possible applications for an implantable flow monitoring device.

There are known implantable blood pressure sensors (from the company Cardiomems™), and restenosis sensors (from the company Instent™—based on measurement of an impedance change as a function of restenosis), as well as actuators for controlled drug delivery such as a microperistaltic pump (from the company MPS microsystems).

By way of further example, stents with blood flow sensors are described in US 2005/0277839A1 based on a surface acoustic wave flow sensor, and WO 1998/029030A1 based on electrode impedance/conductance measurements.

Many sensor designs no longer function if they are overgrown with a bio-layer (even at a very limited depth, e.g. 100 micrometers). Such sensors are also typically positioned near the lumen wall which impairs the sensing ability.

It would be desirable to be able to monitor blood flow away from the lumen wall, but this has the disadvantage that there is a greater occlusion to the blood flow. This is a problem particularly for long term implants.

SUMMARY OF THE INVENTION

The invention is defined by the claims.

According to examples in accordance with an aspect of the invention, there is provided a particular monitoring system for measuring flow in a vessel. The system includes a sensor-actuator device for (capable of) generating a sensor signal representative, or related to a level of flow of a content of the vessel. The system is able to monitor flow away from the edge of a vessel by begin able to deploying the sensor-actuator toward the center of the vessel. To this end the sensor actuator device is mounted to the support device. When flow monitoring does not need to take place, it can be non-deployed so that it does not present an occlusion to the flow.

The system can comprise a controller (14) for controlling actuation of the sensor-actuator and for receiving sensor signals from the sensor-actuator, the controller being configured (adapted) to operate the sensor-actuator device between the non-deployed position and the deployed position; and to receive sensor signals when the sensor-actuator device is in the deployed position.

The intra vascular support device, the sensor-actuator-device preferably are implantable devices. The entire monitoring system can be implantable.

The support device preferably is for positioning against the wall of a vessel.

The intra-vascular support device for example has a length direction, for positioning against a vessel wall in use with its length direction aligned with a vessel direction. By 'direction of a vessel' may be meant a length direction of a (e.g. blood) vessel, i.e. an axial direction of a vessel.

The support device for example comprises a stent. The sensor may be an integral part of the stent which may be implanted with the stent.

The sensor-actuator may comprise an electroactive polymer sensor-actuator. An electroactive polymer sensor-actuator may for instance comprise a material body comprising electroactive polymer (EAP) material, the material being deformable in response to electrical stimulation. By way of example, the sensor-actuator may comprise an ionic polymer membrane sensor-actuator. These are low voltage devices suitable for in-body operation.

Electroactive polymer material sensor-actuators have the advantage of mechanically simple construction and functionality. This contrasts for instance with mechatronic or other electromechanical actuators or sensors. EAPs also allow small form factor, ideal for deployment in vessels such as blood vessels, where avoiding occlusion of the vessel is important. They also have long lifetime, limiting the need for future invasive procedures to replace the device.

The sensor-actuator may comprise a beam, with a first, fixed end connected to the support device, and an opposite, second, free end. The free end projects into the flow when deployed, and the force against the beam exerted by the flow is sensed. This may for example be based on a change in capacitance of the sensor-actuator.

In one example, the second, free end is adapted to be upstream of the first end in use. In this way, the flow lifts the sensor-actuator and it then adopts a new position in equilibrium with the flow. In this way, it may not need to be continuously actuated once in the flow even if it has a rest position (without any external influencing flow) which is in the non-deployed position. In another example, the second, free end is adapted to be downstream of the first end in use. In this way, the flow tends to move the sensor-actuator to the non-deployed position. It may for example be moved to the non-deployed position more quickly.

The beam may be aligned with the length direction of the support device when in the non-deployed position. When deployed, the free end may then pivot radially from the support device into the flow.

The sensor-actuator may have bi-stable actuation. This saves power in that once driven to either of its deployment positions, the sensor-actuator no longer needs to be powered. This bistability may be achieved using a mechanical latching function.

The system typically comprises a battery for providing the power to actuate the sensor-actuator. The controller may be adapted to monitor the battery life, and to provide actuation to the non-deployed position in advance of the battery reaching its end of life. Thus, when the implant reaches the end of its life, it is driven to the non-deployed position to present a minimum occlusion to the flow.

The controller may be adapted to implement simultaneous actuation and sensing by using a relatively low frequency actuation signal and superposing a relatively high frequency sensing signal. This is one way to implement sensing and actuation at the same time, instead of performing time-sequential actuation and sensing.

The sensor-actuator may be an electroactive polymer sensor-actuator in this case, or in other examples a sensor-actuator comprising a different responsive material responsive to electrical stimuli. For the avoidance of doubt, relatively means relative to the other of the frequencies.

The sensor-actuator may comprise at least two pressure sensors spaced along the support device, each having a deployed position and a non-deployed position. This provides an alternative way to derive a flow measurement.

The controller may be adapted to actuate the sensor-actuator to provide vibration for implementing a cleaning function. This is used to prevent clogging of the system.

A look up table may be provided for providing a mapping between sensor signals and a level of flow. This look up table may be populated by a calibration routine. Alternatively, algebraic functions may be used to map between sensor readings and the flow. The lookup table may be used to translate a measured sensor signal to a corresponding level of flow.

The sensor-actuator is preferably in its non-deployed state before and during impanation or insertion in a vessel especially if it is an implantable device. Thus during a use procedure, the device can have a smaller form factor facilitating insertion or implantation.

The controller can include a transmitting device for transmitting the received sensor signal to an external device that is capable of receiving the transmitted signal. The external device is one that is located on the outside of the vessel (e.g. the periphery of a vessel) and preferably outside of a body (e.g. of an animal or human subject) including the vessel.

The external device may be, but need not be part of the monitoring system. Thus, the external device with the transmitting device may be used to retrieve the sensor data without a wired connection, thus preventing the need for holes in a vessel.

The controller and transmitter may be for transmitting the sensor signal in raw format or the controller may be configured to be able to process the sensor data into corresponding level a flow data, e.g. by making use of a lookup table as described herein before. Alternatively, the external device is for receiving the sensor data and has a further controller for processing the sensor signal into a level of flow data.

The transmitting system can be a locally powered one or a remotely powered one. In the first mentioned, the support device includes a battery (fixed or rechargeable). This may be the same one that is used for receiving the sensor data from and powering actuation of the sensor-actuator device. In the second one mentioned, the controller is configured to be able to receive power from the external device when transmitting data and possible also receiving data from the sensor actuator device. Such external power can thus also be sued to actuate the sensor-actuator device.

Either or both of the controller or the further controller can be configured to be connected to a memory for storing the sensor data and/or the level of flow data and if applicable the lookup table. The memory may be local or part of a network such as an internet (LAN, WAN or other).

The external device may have a further transmitting system for further transmitting the sensor signal or level of flow data to one or more other devices. It may have an internet connection (wired or wireless) for such purpose.

The external device may have a user interface at least having a means of providing an output to the user of the sensor signal and/or the level of flow data, e.g. a means in the form of display (for a visual representation), and/or a speaker (for audible representation) and/or a display or other tactile board (for a tactile representation).

The external device may be wearable by a subject, and it may even be implantable under the skin of a subject. In such case it may have a battery (fixed or rechargeable) for powering. It may also be a semi fixed location device with connection to socket powering. This may be useful in home or hospital environment

BRIEF DESCRIPTION OF THE DRAWINGS

Examples of the invention will now be described in detail with reference to the accompanying drawings, in which.

DETAILED DESCRIPTION OF THE EMBODIMENTS

Figure 1:
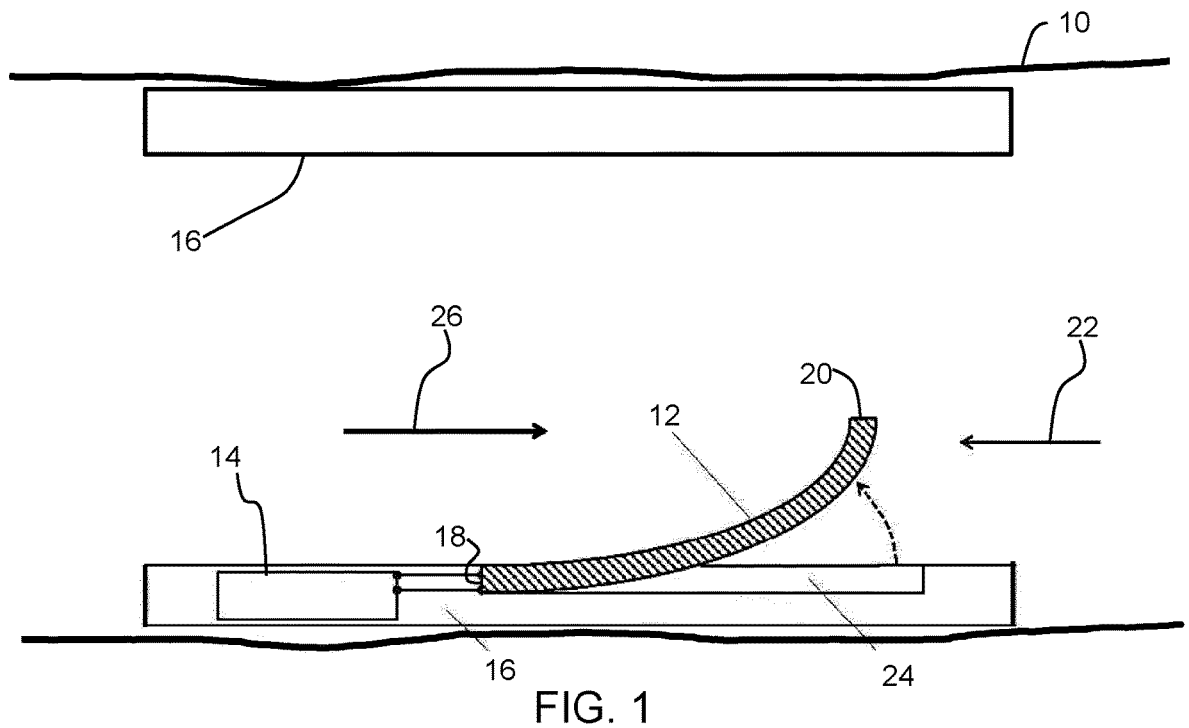
FIG. 1 shows an implantable sensor-actuator system located in a vessel.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides a monitoring system comprising an intra-vascular support device, preferably for positioning against a vessel wall, and a sensor-actuator device mounted to the support device. Both devices are preferably implantable. The sensor-actuator device is drivable between a non-deployed position in which it is against the support device and a deployed position in which it is displaced away from the support device. Sensor signals are preferably generated when in the deployed position. This system is able to monitor flow away from the edge of a vessel by deploying the sensor-actuator towards the center of the vessel. When flow monitoring does not need to take place, it can be non-deployed so that it does not present an occlusion to the flow.

The term vessel is meant to include a tube, possibly narrow, for transporting gaseous and/or fluidic content. Preferably the vessel is part of a body of a subject such as animal, human or plant. Thus e.g. the vessel can be a (narrow) water transporting tube in a plant. More preferably it is a part of the circulatory system and function to transport bodily fluids such as blood or lymphatic fluid (lymph) through a body of a subject. The vessel may thus be blood vessel or part of the lymphatic structure.

FIG. 1 shows an implantable sensor-actuator system located in a vessel 10. The sensor-actuator system comprises a sensor-actuator part 12 and a controller 14. The sensor-actuator is attached to an intra-vascular support device 16 having a length direction, for positioning against the vessel wall with its length direction aligned with the vessel direction as shown. The support device is a stent, graft or a flexible plastic tube in this case. It may however also be part of a catheter type system.

The sensor-actuator 12 is mounted to the support device 16 but also has a portion which extends into the flow within the vessel.

By "sensor-actuator device" is meant a device which can be physically moved or deformed by actuation and which can also sense an external force input at least when at one actuation position. There may be separate actuation components and sensing components, or else a single structure can perform both functions. The force input may be due to a flow of a content in the vessel.

The controller 14 controls actuation of the sensor-actuator and the reception of sensor signals from the sensor-actuator.

In the main examples described below, the sensor-actuator is any device which generates a signal which varies in a predictable way as a function of a degree of bending and which can also be actuated to bend to a particular state.

The deformation of the sensor-actuator device depends on the blood flow velocity which varies with the cardiac cycle and across the blood vessel. The deformation for example causes a varying capacitance, and this capacitance serves as the signal to be sensed.

The sensor-actuator 12 comprises a beam, with a first, fixed end 18 connected to the support device 16, and an opposite, second, free end 20. The sensor-actuator 12 is in one example a flexible passive electroactive polymer (EAP) sensor, in particular an ionic polymer membrane sensor (e.g. IPMC). This operates at low voltage and is suitable for both sensing and actuation within an in-body environment. It has flexible electrodes on both sides. The use of such sensors as flow sensors is known. However, a different type of deformable capacitance sensor may be used, or pressure sensors may also be used (as discussed further below).

Stent diameters typically vary from mm's to cm's depending on the application (peripheral artery disease, coronary artery disease, abdominal aortic aneurysm). The sensor-actuator length may vary accordingly. The sensor-actuator length may be selected such that when actuated into the deformed curved position shown, the free end may reach the center of the vessel.

The controller is used to drive the sensor-actuator between a non-deployed position in which it is against the support device 16 and hence located along the vessel wall, and a deployed position in which it is displaced away from the support device. Sensor signals are received and possibly processed in the deployed position.

FIG. 1 shows the deployed position. The free end 20 projects into the flow when deployed as shown, and the force against the beam exerted by the flow is sensed.

In one example, the second, free end 20 is upstream of the first end in use. In this example the flow is in the direction represented by the arrow 22.

In this way, the flow 22 lifts the sensor-actuator and it adopts the position shown, in which it is in equilibrium with the flow. Even if the sensor-actuator has a bias towards the non-deployed (flat) position when not actuated, once it has been moved to the deployed position it can stay in that position due to the hydrodynamic force exerted by the flow.

In the default position when it is not deployed, and not actuated, the sensor-actuator may lie flat located in a cavity 24, or it may be slightly pre-bent downwards so that the free end 20 of the actuator faces downwardly (i.e. radially outwardly with respect to the vessel) and there is then little risk of fluid penetrating under the sensor-actuator and lifting it up unwantedly.

The sensor-actuator is actuated only briefly when a sensor measurement is desired until its maximum deflection is reached, after which the actuation power is removed and the sensor-actuator is short circuited. This places it into a condition most suitable for sensing. In this configuration the electrical impedance Z is monitored which is indicative of the volume flow rate Q based on calibration information, i.e. $Z=f(Q)$.

When the sensing is complete, the sensor-actuator is actuated with a reversed voltage to return the sensor-actuator to its default position.

This arrangement has a short actuation time requiring a low energy consumption, and it makes use of sequential actuation, then sensing, then actuation which enables simple electronics to be used.

It is possible to use a sensor-actuator with a bi-stable operation mode. The driving signal may again be removed when the actuator has reached the actuated position but without requiring the flow to maintain the sensor-actuator in a given position.

The power savings which can be obtained by avoiding the need for continuous actuation enable the actuator to measure for longer time periods if required.

A short vibration of the sensor-actuator once back into flattened position may be used to remove loose debris which potentially collects in the cavity 24 when the sensor-actuator is in its actuated position.

In another example, the second, free end 20 is downstream of the first end in use. In this example the flow is in the direction represented by the arrow 26. This flow tends to move the sensor-actuator to the non-deployed position. It may for example be moved to the non-deployed position more quickly.

The time required t to return to the default position after actuation relates to the flow rate, $t=f(Q)$.

The electrical impedance may again be a measure for the deformation in that the shape adopted will be a function of the flow. However, the time t to return to the non-deployed position may also be used as the sensed parameter. For this purpose, a conducting pad can be placed in the end of the cavity 24 which acts as a switch for measuring contact. A time interval between the end of actuation and the detection of the contact may then be measured, and this can be converted to a flow, again using calibration information.

The velocity range of the sensor-actuator can be extended by applying different electrical conditions after actuation. For low flow velocity conditions, the sensor-actuator can be short-circuited to improve the recovery back to the flat state. For high flow velocity conditions, the sensor-actuator can be held with open circuit conditions (or a defined impedance value) to partly impede the recovery of the sensor-actuator and resist the stronger flow.

It may be desirable to ensure the sensor-actuator adopts the non-deployed position when at the end of life of the implant, which is for example when the battery runs out. If the sensor-actuator is in the deployed state for a prolonged period of time there is a chance of it being in this state at the end of life and then causing a (partial) blockage in the stent. In order to prevent this situation, a battery monitoring system is used to indicate when the end of the battery life is approaching, and then to use the remaining battery power to safely return the actuator to a position parallel to the stent wall before the battery is finally empty.

For the example in which the free end faces into the flow (i.e. flow 22) a slightly greater actuation may be used at the end-of-life than simply to achieve the flat end position, so that the free end of the actuator is facing downwards and there is less risk of fluid flow lifting it up, even if the actuator relaxes slightly after the last actuation. This additional safety feature may be of interest since there is no battery power left to make any corrections.

There may be simultaneous sensing and actuation. For an IMPC sensor-actuator, this can be achieved by measuring the impedance of the outer electrodes separately to the actuation voltage or adding a high frequency signal to the quasi-DC actuation signal. The approach of combining a DC actuation signal with a high frequency superposed AC signal for sensing is described in detail in WO 2017/036695. Although more power consuming, the accuracy of the flow measurement may be improved using these methods as the velocity profile can be determined at any point between zero deflection (corresponding to the vessel wall) up to full deflection (for example corresponding to the middle of the vessel). In this way, sensing may be performed at different intermediate actuation states, rather than actuating fully to one or other of two bi-stable states. A velocity profile may then be obtained across the diameter of the vessel. In this way, additional measurement features are also possible: for instance, asymmetry in the flow profile can be determined.

This approach also means that the flow itself is not relied upon to maintain the sensor-actuator in an operative position. As a result, the sensing is robust to significant changes in flow velocity, because the flow is not an essential design parameter in the sensor operation.

Figure 2:
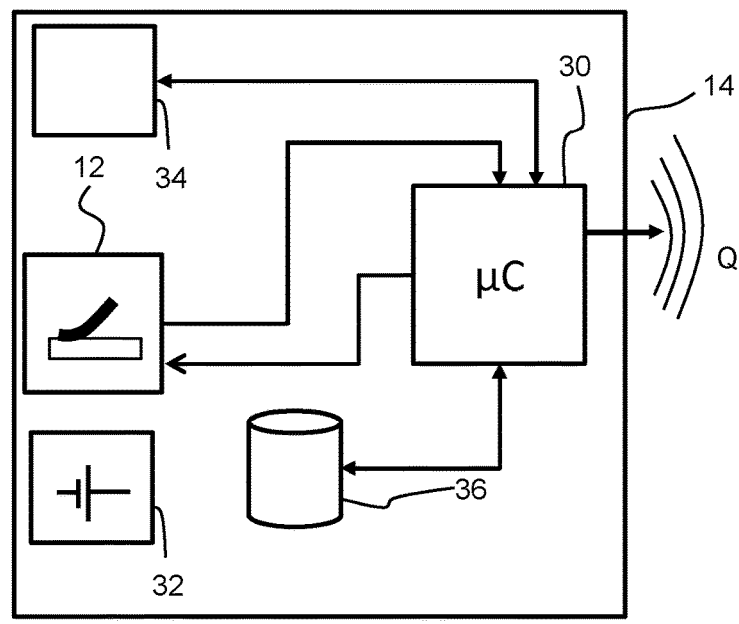
FIG. 2 shows the control circuit in more detail.

FIG. 2 shows one example of the components of the controller 14.

The sensor-actuator 12 is controlled (i.e. actuated) by a processor 30, which also receives and processes the sensor signals. The controller 14 has an internal battery 32 and a memory 34. The processor is able to provide the sensor information (e.g. flow rate Q) over a wireless connection to an external interrogation unit (not shown).

There are various options for the amount of data storage and processing capability which is implanted and the amount which is external. For example, the implanted sensor-actuator may only output raw sensing signals, such as impedance values, or else it may generate flow values. There are also various options for how much energy storage capability is implanted and how much is received by way of wireless energy transfer, in particular for providing energy for providing actuation and for providing the energy for processing the sensor signals.

By way of example, a first option is to continuously collect and record sensing information in the implanted device as well as providing local power for the actuation. In this case, a (rechargeable) battery is used to provide local power. Wireless powering may then be used to charge the battery, for example over night by wearing a charging belt. Furthermore, the wireless coupling may be used to read out the stored data if the implant is not provided with active transmitting functionality. Alternatively, the implant may have locally powered wireless data transmission capability.

A second option is to measure (and optionally process) sensor data only on demand for example if the user places a wireless transmitter (as part of an external device), which includes wireless powering, above the implant. This may be appropriate if data is only needed for a regular check a few times during the day.

Thus it is possible to have an implanted power source or to provide power wirelessly, as well as having different possible levels of data processing and storage in the implanted device.

One example of a basic implanted device would comprise a microcontroller (including memory and software) which controls a driver of the sensor-actuator and also generates an AC sensing signal. The sensing signal may either be superimposed to the DC actuation signal or provided from an independent AC oscillator. The device additionally has a means to measure the impedance, and this impedance functions as the sensor signal, This could simply be a series resistance, and the voltage drops and phase shifts are measured by the microcontroller.

The processor 30 may determine the flow Q based on a look up table 36. The flow velocity is for example obtained from the varying capacitance C (or other impedance measurement) of the sensor-actuator $C=f(v)$.

The look up table 36 thus provides a mapping between the sensor signals and a level of flow. There may be different sub-tables for different actuation levels, for example when different flow measurements are obtained for different locations across the vessel area as discussed above. This look up table may be populated by a calibration routine. Alternatively, algebraic functions may be used to map between sensor readings and the flow.

The local flow velocity can be translated to a volumetric flow rate based on the known cross sectional area of the lumen and an assumed flow type (e.g. laminar, turbulent). Alternatively, a more accurate volumetric flow can be based on multiple flow measurements at different parts of the cross sectional area of the vessel.

The memory 34 may be used for storing either the raw sensor values or the flow information.

Before and during implantation, the stent with its integral sensor-actuator is folded in a delivery catheter, with the sensor-actuator in the non-deployed position.

The example above shows a single sensor. There may also be multiple sensors on the stent, and differences in response may then be analyzed. Endothelium overgrowth would be more homogenous than the formation of plaque. From monitoring the differences, the build-up of plaque vs. endothelium overgrowth can be assessed. There may be multiple sensors around the circumference and/or in the axial direction.

There are various options for wireless connection to the implanted sensor, to provide a communication channel. The wireless connection may also be used for energy transfer, for example to recharge a local energy source (battery or capacitor) or to provide power directly to sensor-actuator.

In general an implant, whether passive or active, may be powered in many ways (the power being for actuation and/or communication). Depending on the functionality and operation mode of the implant, different requirements for the energy source are present.

For a continuous active function, such as a requirement for active mechanical actuation in order to generate an output signal, there is a higher energy requirement than for a passive temporally limited (e.g. on-demand) function, such as the occasional read out of an active sensor. However in both cases, there is a need for either a wired connection to a local power source, or a wireless coupling to a power transmitter.

Delivering electrical power to medical implants for powering or communication is a topic which is well-described in literature.

Comprehensive reviews of power aspects for implantable medical devices are given in B. A. Achraf, A. B. Kouki and C. Hung, "Power Approaches for Implantable Medical Devices," sensors, no. 28889-28914; doi:10.3390/s151128889, 2015, J. Lee, J. Jang and Y.-K. Song, "A review on wireless powering schemes for implantable microsystems in neural engineering applications," Biomed Eng Letters, no. DOI 10.1007/s13534-016-0242-2, pp. 6:205-215, 2016, A. Kim, M. Ochoa, R. Rahim and B. Ziaie, "New and Emerging Energy Sources for Implantable Wireless Microdevices," IEEE: SPECIAL SECTION ON NANO-BIOSENSORS, no. 10.1109/ACCESS.2015.2406292, 2014, and K. N. Bocan and E. Sejdi'c, "Adaptive Transcutaneous Power Transfer to Implantable Devices: A State of the Art Review," sensors, vol. 16, no. doi:10.3390/s16030393, p. 393, 2016.

Any of these solutions may be used to provide power or a communications channel to the implant, and some approaches will be discussed below.

A first approach is to provide a wired power source as part of the implant, as described above. A wired power source may be an ordinary battery (non-rechargeable or rechargeable) such as shown as 32, directly connected to the implant or to its operating electronics. However, since implants usually will be worn over a long period of time, a high capacity and high energy density battery would be of benefit. The power density of (re-chargeable) batteries is expected to grow further making them increasingly suitable for long term monitoring functions.

Instead of conventional batteries, bio-fuel cells or nuclear batteries may be applicable. Another alternative power source, which is very similar to a battery, is a super capacitor, which is a capacitor having an extremely high capacitance and a very low self-discharge characteristic.

Energy harvesters may instead be used to operate any implant. Accordingly a power generator could for example be operated by human body energy such as motion of an extremity but also motion of an inner organ or any dynamics resulting from a fluid flow (blood in an artery) or gas (air in a lung). The power generator may be able to store energy in a super capacitor or re-chargeable battery, and/or be able to directly operate an implant.

An energy harvester does not necessarily need to be in close vicinity to the implant itself but could also be spatially separated. A wired connection may be used between them. Also in the field of energy harvesters, efforts are being made to make them smaller and more efficient in order to make them more attractive as an internal (and everlasting) energy source for medical devices.

Wireless energy transmission systems may be classified according to the physical coupling mechanism, which can be either capacitive, inductive (magnetic) or electromagnetic. All three mechanisms have their own pros and cons and preferred applications. In general, the performance of each approach depends very much on specific boundary conditions such as e.g. the size of the transmitter- and receiver-element (which can be a plate, an inductor or an antenna) and the distance and medium between both elements, as well as their orientation with respect to each other.

An additional smart feature of all wireless power systems is the intrinsic ability of a bidirectional data communication between a transmitter and a receiver.

In applications where low energy levels at short distances need to be transmitted, capacitive coupling may be used. Low to medium power levels at medium to long range may be preferably realized via an electromagnetic coupling. Highest power levels at short distances may be transmitted via an inductive coupling, making use of magnetic fields.

A most basic approach only enables sensor data to be gathered when the external controller is present, in particular if wireless power transfer is used to provide the energy needed for actuation. However, using such a wireless powering technique would not necessarily imply the need to wear such a transmitter continuously to perform the intended use of the implant. For example, an implant may only need to be operated during certain treatments (in e.g. a hospital) or it may only need to be activated at predefined moments in time (e.g. morning, afternoon, evening).

An alternative use case would be to use such a wireless transmitter overnight, to charge an implanted power source, which would be used to operate an implant during the day. This is a hybrid approach where there is a local energy supply so sensor data can be gathered and stored in memory without an external controller in place, but it has a short duration so needs recharging periodically.

The implanted wireless receiver unit and the implanted sensor-actuator may be spatially separated from each other. For example, the receiving element, e.g. a receiver inductance may be located directly underneath the skin, in order to realize a strong coupling between the transmitter and receiver and thus to maximize the energy transmission efficiency and to minimize the charging time of an implanted battery. Of course, this would require a more involved implantation procedure than if the implanted elements are fully integrated into the stent (or other support structure).

There are also options which do not rely on electrical energy to realize a wireless energy transmission system, in particular making use of optical, ultrasonic or mechanical pressure waves.

The example above is based on the use of a sensor-actuator with a deflection sensor function for measuring flow. An alternative is to use pressure sensors. For example a pressure sensor before and after a stent can measure the pressure drop over the stent, which indicates the flow rate under ideal conditions. Alternatively, based on constant upstream conditions (pressure and flow rate), the pressure after the stent side indicates the downstream flow resistance in the blood vessel. Thus, there may be two pressure sensors attached to EAP actuators which are operated as described above. In this case, the sensor-actuator has separate physical parts for the sensor function (pressure sensor) and for the actuator function (EAP actuator). The term "sensor-actuator" should be understood accordingly.

As discussed above, a controller performs the data processing. The controller can be implemented in numerous ways, with software and/or hardware, to perform the various functions required. A processor is one example of a controller which employs one or more microprocessors that may be programmed using software (e.g., microcode) to perform the required functions. A controller may however be implemented with or without employing a processor, and also may be implemented as a combination of dedicated hardware to perform some functions and a processor (e.g., one or more programmed microprocessors and associated circuitry) to perform other functions.

Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media such as volatile and non-volatile computer memory such as RAM, PROM, EPROM, and EEPROM. The storage media may be encoded with one or more programs that, when executed on one or more processors and/or controllers, perform the required functions. Various storage media may be fixed within a processor or controller or may be transportable, such that the one or more programs stored thereon can be loaded into a processor or controller.

As mentioned above, the sensor-actuator may be implemented using an electroactive polymer (EAP) device. EAPs are an emerging class of materials within the field of electrically responsive materials. EAPs can work as sensors or actuators and can easily be manufactured into various shapes allowing easy integration into a large variety of systems.

Materials have been developed with characteristics such as actuation stress and strain which have improved significantly over the last ten years. Technology risks have been reduced to acceptable levels for product development so that EAPs are commercially and technically becoming of increasing interest. Advantages of EAPs include low power, small form factor, flexibility, noiseless operation, accuracy, the possibility of high resolution, fast response times, and cyclic actuation.

The improved performance and particular advantages of EAP material give rise to applicability to new applications.

An EAP device can be used in any application in which a small amount of movement of a component or feature is desired, based on electric actuation or for sensing small movements.

The use of EAPs enables functions which were not possible before, or offers a big advantage over common sensor and actuator solutions, due to the combination of a relatively large deformation and force in a small volume or thin form factor, compared to common actuators. EAPs also give noiseless operation, accurate electronic control, fast response, and a large range of possible actuation frequencies, such as 0-1 MHz, most typically below 20 kHz.

Devices using electroactive polymers can be subdivided into field-driven and ionic-driven materials.

Examples of field-driven EAPs include Piezoelectric polymers, Electrostrictive polymers (such as PVDF based relaxor polymers) and Dielectric Elastomers. Other examples include Electrostrictive Graft polymers, Electrostrictive paper, Electrets, Electroviscoelastic Elastomers and Liquid Crystal Elastomers.

Examples of ionic-driven EAPs are conjugated/conducting polymers, Ionic Polymer Metal Composites (IPMC) and carbon nanotubes (CNTs). Other examples include ionic polymer gels.

Field-driven EAPs are actuated by an electric field through direct electromechanical coupling. They usually require high fields (tens of megavolts per meter) but low currents. Polymer layers are usually thin to keep the driving voltage as low as possible.

Ionic EAPs are activated by an electrically induced transport of ions and/or solvent. They usually require low voltages but high currents. They require a liquid/gel electrolyte medium (although some material systems can also operate using solid electrolytes).

Both classes of EAP have multiple family members, each having their own advantages and disadvantages.

A first notable subclass of field driven EAPs are Piezoelectric and Electrostrictive polymers. While the electromechanical performance of traditional piezoelectric polymers is limited, a breakthrough in improving this performance has led to PVDF relaxor polymers, which show spontaneous electric polarization (field driven alignment). These materials can be pre-strained for improved performance in the strained direction (pre-strain leads to better molecular alignment). Normally, metal electrodes are used since strains usually are in the moderate regime (1-5%). Other types of electrodes (such as conducting polymers, carbon black based oils, gels or elastomers, etc.) can also be used. The electrodes can be continuous, or segmented.

Another subclass of interest of field driven EAPs is that of Dielectric Elastomers. A thin film of this material may be sandwiched between compliant electrodes, forming a parallel plate capacitor. In the case of dielectric elastomers, the Maxwell stress induced by the applied electric field results in a stress on the film, causing it to contract in thickness and expand in area. Strain performance is typically enlarged by pre-straining the elastomer (requiring a frame to hold the pre-strain). Strains can be considerable (10-300%). This also constrains the type of electrodes that can be used: for low and moderate strains, metal electrodes and conducting polymer electrodes can be considered, for the high-strain regime, carbon black based oils, gels or elastomers are typically used. The electrodes can be continuous, or segmented.

A first notable subclass of ionic EAPs is Ionic Polymer Metal Composites (IPMCs). IPMCs consist of a solvent swollen ion-exchange polymer membrane laminated between two thin metal or carbon based electrodes and requires the use of an electrolyte. Typical electrode materials are Pt, Gd, CNTs, CPs, Pd. Typical electrolytes are Li+ and Na+ water-based solutions. When a field is applied, cations typically travel to the cathode side together with water. This leads to reorganization of hydrophilic clusters and to polymer expansion. Strain in the cathode area leads to stress in rest of the polymer matrix resulting in bending towards the anode. Reversing the applied voltage inverts bending. Well known polymer membranes are Nafion® and Flemion®.

Another notable subclass of Ionic polymers is conjugated/conducting polymers. A conjugated polymer actuator typically consists of an electrolyte sandwiched by two layers of the conjugated polymer. The electrolyte is used to change oxidation state. When a potential is applied to the polymer through the electrolyte, electrons are added to or removed from the polymer, driving oxidation and reduction. Reduction results in contraction, oxidation in expansion.

In some cases, thin film electrodes are added when the polymer itself lacks sufficient conductivity (dimension-wise). The electrolyte can be a liquid, a gel or a solid material (i.e. complex of high molecular weight polymers and metal salts). Most common conjugated polymers are polypyrrole (PPy), Polyaniline (PANi) and polythiophene (PTh).

An actuator may also be formed of carbon nanotubes (CNTs), suspended in an electrolyte. The electrolyte forms a double layer with the nanotubes, allowing injection of charges. This double-layer charge injection is considered as the primary mechanism in CNT actuators. The CNT acts as an electrode capacitor with charge injected into the CNT, which is then balanced by an electrical double-layer formed by movement of electrolytes to the CNT surface. Changing the charge on the carbon atoms results in changes of C—C bond length. As a result, expansion and contraction of single CNT can be observed.

For the sensing functionality, the use of capacitance change is discussed above, in particular in connection with an ionic polymer device. For field driven systems, a capacitance change can also be measured directly or by measuring changes in electrode resistance as a function of strain.

Piezoelectric and electrostrictive polymer sensors can generate an electric charge in response to applied mechanical stress (given that the amount of crystallinity is high enough to generate a detectable charge). Conjugated polymers can make use of the piezo-ionic effect (mechanical stress leads to exertion of ions). CNTs experience a change of charge on the CNT surface when exposed to stress, which can be measured. It has also been shown that the resistance of CNTs change when in contact with gaseous molecules (e.g. $O_2$, $NO_2$), making CNTs usable as gas detectors.

Sensing may also be based on force measurements and strain detection. Dielectric elastomers, for example, can be easily stretched by an external force. By putting a low voltage on the sensor, the strain can be measured as a function of voltage (the voltage is a function of the area).

The main example of interest is for monitoring a subject after insertion of a stent. Stent placement may be in a coronary artery, with the risk that the stent becomes blocked again due to restenosis or due to the formation of scar tissue. Stent placement may instead be in the lower leg to open-up a blocked artery caused by peripheral artery disease. The blood flow pattern is then disrupted and there is a risk that in the treated artery the blood flow suddenly increases due to which another artery suddenly receives less flow ("vascular steal"). Flow monitoring is able to determine this.

However, other examples where flow monitoring is of interest are presented above. The invention for example may be applied to stents, to stent grafts, heart valves, coronary arterial bypass grafts and shunts.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A monitoring system for measuring flow in a vessel, the monitoring system comprising:
   an intra-vascular support device for positioning within the vessel;
   a sensor-actuator device for generating a sensor signal related to the flow, the sensor-actuator device being mounted to the intra-vascular support device and operable between a non-deployed position in which it is against the intra-vascular support device and a deployed position in which it is displaced away from the intra-vascular support device; and
   a controller for controlling actuation of the sensor-actuator device and for receiving the sensor signal from the sensor-actuator device, the controller being configured to:
      operate the sensor-actuator device between the non-deployed position and the deployed position; and
      receive the sensor signal when the sensor-actuator device is in the deployed position.

2. The monitoring system of claim 1, wherein the intra-vascular support device is for positioning against a wall of the vessel.

3. The monitoring system of claim 1, wherein the intra-vascular support device and the sensor-actuator device are implantable devices.

4. The monitoring system of claim 1, wherein the intra-vascular support device comprises a stent.

5. The monitoring system of claim 1, wherein the sensor-actuator device comprises an electroactive polymer sensor-actuator.

6. The monitoring system of claim 1, wherein the sensor-actuator device comprises a beam, with a first, fixed end connected to the intra-vascular support device, and an opposite, second, free end.

7. The monitoring system of claim 6, adapted:
   to be placed in the vessel such that the opposite, second, free end is upstream of the first, fixed end, or
   to be placed in the vessel such that the opposite, second, free end is downstream of the first fixed end.

8. The monitoring system of claim 1, wherein the sensor-actuator device has bi-stable actuation.

9. The monitoring system of claim 1, further comprising a battery for providing power to actuate the sensor-actuator device, wherein the controller is adapted to monitor the battery life, and to provide actuation to the sensor-actuator device in the non-deployed position in advance of the battery reaching its end of life.

10. The monitoring system of claim 1, wherein the controller is adapted to implement simultaneous actuation and sensing by using a relatively low frequency actuation signal and superposing a relatively high frequency sensing signal.

11. The monitoring system of claim 1, wherein the sensor-actuator device comprises at least two pressure sensors spaced along the intra-vascular support device, each of the at least two pressure sensors having a deployed position and a non-deployed position.

12. The monitoring system of claim 1, wherein the controller is adapted to actuate the sensor-actuator device to provide vibration for implementing a cleaning function.

13. The monitoring system of claim 1, wherein the controller comprises a transmitter and is further configured to:
   transmit the received sensor signal to an external device for receiving the transmitted sensor signal; or
   process the received sensor signal in a corresponding data signal representing a level of flow and transmit the data signal to an external device for receiving the transmitted data signal.

14. The monitoring system of claim 1, further comprising a look up table for providing a mapping between sensor signals and corresponding levels of flow.

15. The monitoring system of claim 13, further comprising the external device.

16. The monitoring system of claim 15, wherein the external device further includes a user interface for providing, to a user, an output of the sensor signal and/or the level of flow.

* * * * *